United States Patent [19]

Holtermann et al.

[11] Patent Number: 5,626,569

[45] Date of Patent: May 6, 1997

[54] DEVICE FOR VENTING AND CONTROLLING THE PRESSURE INSIDE A STOMA COLLECTION BAG

[75] Inventors: Henri Holtermann, Saint-Jean-de-Luz; Claude Hamelin, Ascain, both of France

[73] Assignee: B. Braun Biotrol, Boulogne Billancourt, France

[21] Appl. No.: 333,643

[22] Filed: Nov. 3, 1994

[30] Foreign Application Priority Data

Nov. 8, 1993 [FR] France .................. 93 13246
May 11, 1994 [FR] France .................. 94 05805

[51] Int. Cl.$^6$ .................................. A61F 5/44
[52] U.S. Cl. ............... 604/333; 604/332; 55/385.4; 251/262
[58] Field of Search .................. 604/332, 333, 604/335, 337; 55/385.4, 504, 505, 511; 251/228, 262

[56] References Cited

U.S. PATENT DOCUMENTS

| | | |
|---|---|---|
| 3,865,109 | 2/1975 | Elmore et al. . |
| 4,232,672 | 11/1980 | Steer et al. ............... 604/333 |
| 4,268,286 | 5/1981 | Steer et al. ............... 604/333 |
| 4,387,671 | 6/1983 | Jarvis ....................... 55/505 |
| 4,451,258 | 5/1984 | Jensen . |
| 4,516,974 | 5/1985 | Davis ....................... 604/333 |
| 4,938,749 | 7/1990 | Jensen ...................... 604/333 |
| 4,957,518 | 9/1990 | Brassell ................... 55/385.4 |
| 5,304,157 | 4/1994 | Brooks et al. ............. 604/333 |
| 5,372,594 | 12/1994 | Colacello et al. .......... 604/335 |

FOREIGN PATENT DOCUMENTS

| | | |
|---|---|---|
| 116363 | 3/1987 | European Pat. Off. . |
| 294257 | 10/1991 | European Pat. Off. . |
| 1381556 | 11/1964 | France ...................... 55/505 |
| 2514636 | 4/1983 | France . |
| 3304311 | 8/1984 | Germany . |
| 1416594 | 12/1975 | United Kingdom . |
| 2094153 | 9/1982 | United Kingdom . |
| 2116433 | 9/1983 | United Kingdom . |

Primary Examiner—Mark O. Polutta
Attorney, Agent, or Firm—Bell, Seltzer, Park & Gibson, P.A.

[57] ABSTRACT

A vent device, in particular for a stoma bag, constituted by an essentially flat housing comprising a base having a face inside the housing and a face outside the housing, and adapted to be fixed via said outside face to an exposed face of said bag and provided with an opening communicating with said bag, and also provided with a valve of the type that is closed at rest, the valve being formed by a valve member adapted to bear against the inside face of said opening in said base, and being integral with resilient means for urging said valve member against said base with a predetermined return force, wherein the housing further includes a removable cover adapted to close said base and wherein the valve member is secured to said cover.

19 Claims, 7 Drawing Sheets

DEVICE FOR VENTING AND CONTROLLING THE PRESSURE INSIDE A STOMA COLLECTION BAG

FIELD OF THE INVENTION

The invention relates to a device for venting and controlling the pressure inside a stoma collection bag, and to a bag provided with such a device.

BACKGROUND OF THE INVENTION

As can be seen, for example, in GB-1-416 594 or U.S. Pat. No. 3,865,109, numerous embodiments are already known of stoma collection bags provided with venting devices that serve both to exhaust intestinal gases that have penetrated into the bag, and to maintain a residual pressure level inside the bag opposing any tendency of the component films or sheets of the bag to stick to each other, which would prevent satisfactory collection of solid or liquid excreta. This applies in particular to the device of patent application FR 2 514 636 which comprises a valve body provided with two facing orifices, one communicating with the inside of the bag and surrounded by a valve seat, the other communicating with the outside. Inside the body, between the two orifices, there is a shutter element for the valve in the form of a disk which is provided at its periphery of a plurality of resilient tongues that bear against the inside wall of the valve body and press the shutter element against the valve seat.

Collection bags are also known, e.g. from EP-B1-0 294 257 or EP-A-0 116 363 which are provided not only with venting devices but also with filters placed inside or outside the bag and of a thickness that is maintained at a value that is as small as possible so as to enable them to perform their function while having little effect on the extent to which the bag projects from the body underneath the clothes of a user. However, insofar as known devices, and in particular those known from the two last-mentioned documents, are integrated in the bag to which they are fitted, they cannot be used without a filter, nor they can be made operational either automatically (i.e. without intervention of the patient wearing the bag), or under deliberate control of the patient. As a result, they do not present the characteristics of flexibility in use that are required for fitting to patients either as a function of their own requirements or as a function of the requirements of medical personnel, or to be able to take into account the very different conditions under which a collection bag can be used.

Consequently, the problem arises of providing a device for venting and controlling the pressure inside a stoma collection bag that is suitable for mitigating the drawbacks recalled above.

OBJECTS AND SUMMARY OF THE INVENTION

In general terms, an object of the invention is to provide a device for venting and controlling the pressure inside a stoma collection bag that enables the problem posed to be solved.

Another object of the invention is to provide such a device which is simple to use and as a result can be used by any patient who has been subjected to a surgical operation such as colostomy or ileostomy.

Another object of the invention is to provide such a device that is free form any risk of misfunctioning, which can give rise to situations that are highly embarrassing for patients who have been subjected to surgical operations of the type mentioned above.

Yet another object of the invention is to provide such a device in which manufacturing constraints, in particular the making of its component parts and the assembly thereof, are compatible with industrial manufacture.

Finally, an object of the invention is to provide a stoma collection bag to which a device of the type defined above can easily be associated.

This problem is solved by a vent device, in particular for a stoma bag, constituted by an essentially flat housing comprising a base having a face inside the housing and a face outside the housing, and adapted to be fixed via said outside face to an exposed face of said bag and provided with an opening communicating with said bag, and also provided with a valve of the type that is closed at rest, the valve being formed by a valve member adapted to bear against the inside face of said opening in said base, and being integral with resilient means for urging said valve member against said base with a predetermined return force, wherein the housing further includes a removable cover adapted to close said base and wherein the valve member is secured to said cover.

Thus, manufacture of the present device is facilitated compared with manufacture of the device taught in above-mentioned patent application FR 2 514 636.

No use is made of an independent valve member to be inserted in a valve body even though the small size thereof makes it difficult to handle. As a result assembly can be performed in a factory, e.g. merely by engaging the cover on the base of the housing. It can also be performed by users themselves. The simplification or absence of factory assembly gives rise to a saving in manufacturing cost that is particularly advantageous given the large number of devices manufactured.

Advantageously, the resilient means are constituted by at least one resiliently deformable flat extending between said cover and said valve member. Such a flat is easily obtained by making said base and said cover in the form of a one-piece blank, preferably by injection molding a plastics material, bridges of material in the blank connecting said base to said cover in such a manner that the distance between said cover and said valve member is greater than the distance between said base and said cover in the final housing obtained by breaking said bridges of material and closing said base with said cover.

On request, a filter including a central hole is received in said housing in such a manner as to be clamped between said valve member and said base, its hole being in register with said opening through said base. Where appropriate, users may themselves place the filter in the vent. This may be done while a bag is being worn. This provides great flexibility in use.

Advantageously, the assembly formed by said cover and said closure member is shaped to enable said valve member to be actuated by hand. This is advantageously obtained by a device wherein
  said housing is cylindrical; and
  said cover is secured to said base in such a manner as to be displaced relative to said base by manual actuator means by rotation about the axis (A) of the housing.

It is then preferable for the cover to be secured to the base by mutual engagement, and for the manual actuation means to be constituted by a radially-projecting lug on the cover.

It can then be useful to provide another radially projecting lug on said base suitable for serving as a positioning mark for the lug on the cover. This structure is particularly adapted to the need for the device to be flat so as to remain discrete beneath clothing. It is then easy to push the lug of the cover so as to cause it to rotate at any time while the user is wearing the bag.

In a first embodiment, said valve member is secured to at least one radial finger suitable for moving, when said manual actuation means are actuated, along a circumferentially-extending guide of said base having a shape such that, depending on its position in said guide, said finger can be free or can be raised against said resilient means along a ramp of the guide.

Advantageously, there also exists a position in which said finger can be locked beneath a hook of said guide.

It follows that when the user rotates the cover relative to the base by causing the finger to move along the ramp, the closure member is displaced axially, thereby opening the vent valve member. This disposition is particularly well adapted to the need to be discrete which means that the axial displacement to be provided must be small since the overall thickness of the device must itself be small. The structure provided herein makes such a small displacement possible, even if rotation of the cover is larger and therefore easier to implement.

In a second embodiment, said valve member is constituted by a tapering tip, the cover also including at least one projection while said base includes at least one helical ramp on which said projection is suitable for traveling between a low position and a high position when the cover is rotated relative to said base in such a manner that, in the low position, said tapering tip is urged by the resilient means to close said opening whereas, in the high position, said tip is pushed away from the opening against said resilient means.

Advantageously, there are three projections and three ramps disposed in radial directions that are at 120° intervals relative to one another.

Also advantageously, said projections are integral with a stud which carries said tapering tip at its end, the free ends of said projections being set back relative to said tip so that said tip penetrates into said opening when said projections are in their low position.

As in the first embodiment, rotating the cover causes the valve needle to move axially, thereby opening the valve member.

In this second embodiment, said housing includes an inside space suitable for receiving a filter and defined by a cylindrical wall including axial recesses communicating with top windows of the cover such that the gases can escape in spite of the presence of a filter inside the housing. It is then advantageous for the base to have an internal portion in relief adapted to clamp the filter in such a manner that the gases are constrained to pass through the filter in order to escape via the recesses and the windows.

Advantageously, the cover is secured to the base by a bayonet-type fastening. To do this, said base and said cover preferably have rims suitable for co-operating in such a manner that, once said base and said cover are engaged, said rims co-operate to prevent them from coming apart, said rims each extending over a sector of about 90° and being disposed diametrically opposite each other on the cover and on the base. It is then possible for the cover to penetrate inside the base, the rims of the cover projecting outwards while the rims of the base project inwards. At least one rim is extended by an axial column acting as a stop to prevent the base and the cover rotating beyond a certain amount, thereby ensuring that the projections do not move off said respective ramps.

The invention also provides a stoma collection bag including a device for venting and controlling the pressure inside the bag, as defined above.

BRIEF DESCRIPTION OF THE DRAWINGS

The invention will be well understood from the following description, given by way of example and made with reference to the accompanying drawings, in which.

DETAILED DESCRIPTION

A first embodiment of the device of the invention 10 for venting and controlling the pressure inside a stoma collection bag P is shown in FIGS. 1 to 7. It is designed to be fixed on the exposed face of the bag which, being of the discardable type or of the emptyable type, is generally constituted by two sheets of films $f_1$ and $f_2$ of a plastics material that is impermeable to odors, which films are welded together around their periphery s. In conventional manner, one of the films $f_1$, $f_2$ includes an opening O suitable for being put into communication with the stoma when the bag is applied to the body of the patient, either by means of a coupling system, or by means of an adhesive plate, or by means of a belt, or else by a combination of those various means. The bag P which collects solid or liquid excreta also collects intestinal gases which must be exhausted in order to avoid the bag increasing excessively in volume. However a certain amount of residual pressure must be maintained inside the bag in order to mitigate the drawback that would result if the two films $f_1$ and $f_2$ were to move towards each other and become stuck together which would hinder entry into the bag via the opening O of the solid or liquid excreta to be collected.

Figure 2:
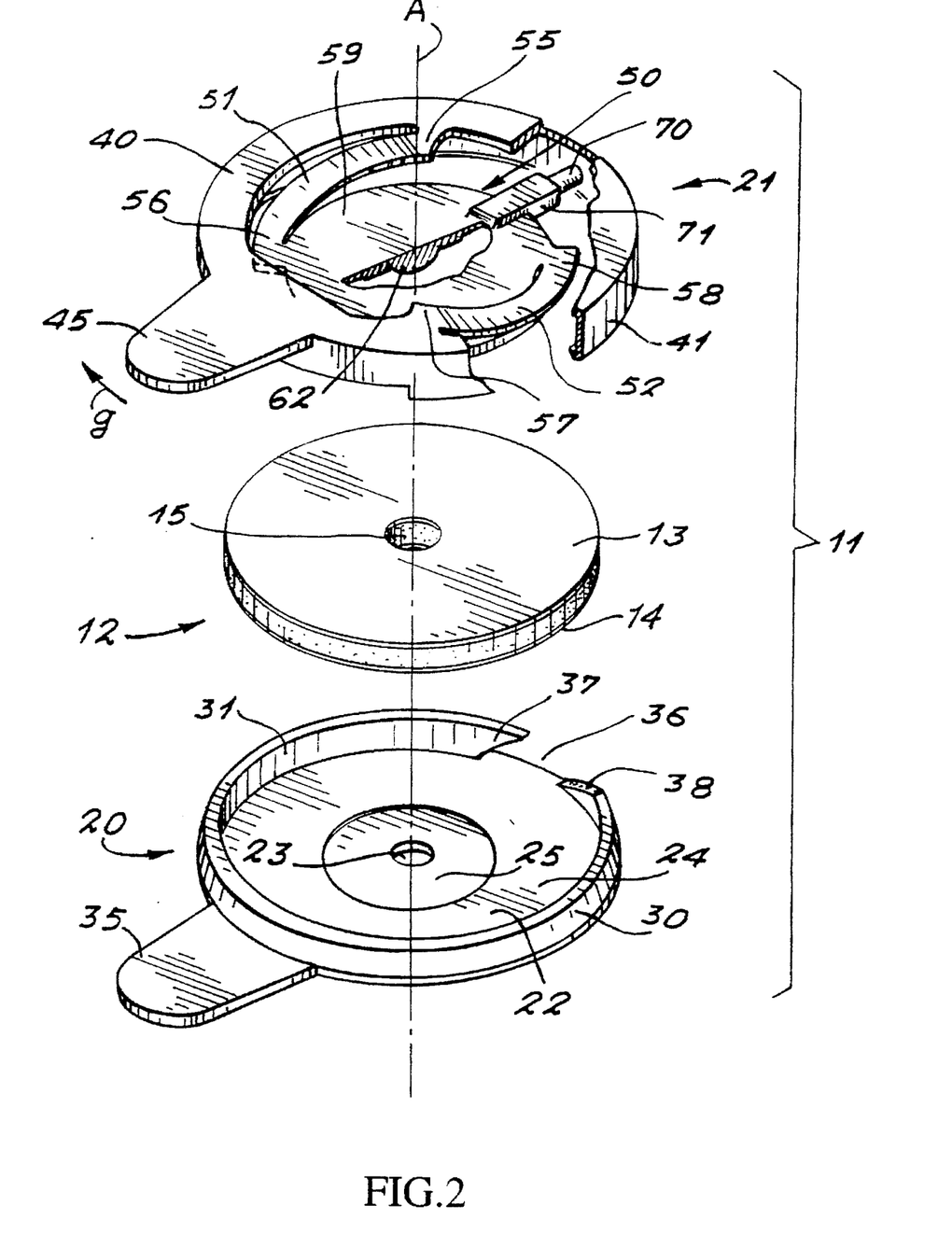
FIG. 2 is an exploded perspective view of the FIG. 1 device in which a cover is shown in a partially cutaway view.

For this purpose, the device of the invention 10 as shown in FIG. 2 essentially comprises a flat housing 11 (typical thickness 5 mm), in which there can be received an odor-absorbing filter 12 made on the basis of a porous substrate such as a foam, or a woven or non-woven cloth impregnated with active carbon or with some other odor-removing agent and shaped to form a thin disk which is covered on both of its faces with a respective gas-impermeable film 13 and 14, the assembly having a central hole 15.

Figure 7:
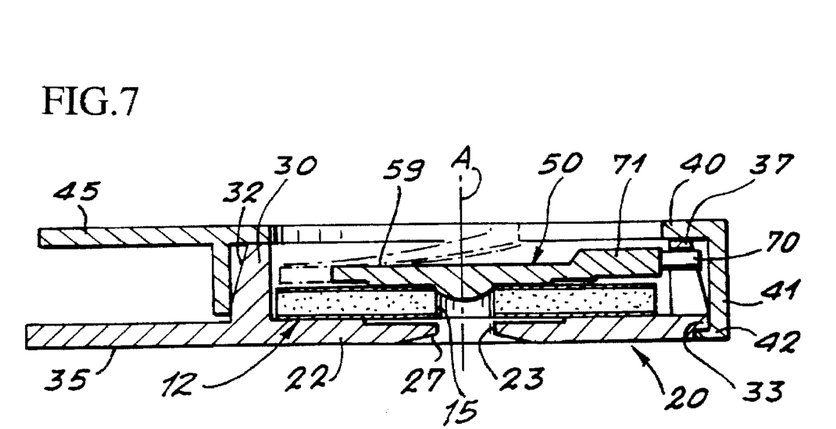
FIG. 7 is a section view on broken line 7—7 of FIG. 4.

The housing 11 is the result of assembling together a base 20 and a cover 21 that are advantageously made by molding, preferably injection molding, an elastically deformable plastics material such as polyethylene, polyamide, ABS, . . . , etc., the base and the cover being connected together by a thin fillet of material until they are separated. The general shape of the housing 11 is that of a cylinder about the axis A (and having a diameter of about 30 mm), and the surfaces of its elements that are to be found inside the housing are referred to below as "inside" surfaces whereas its other surfaces are referred to as being "outside" surfaces. The base 20 which is designed to be fixed on the exposed face of the bag, e.g. via annular welding S or by means of adhesive, includes a plane portion 22 of circular outline that is pierced in its center by an opening 23 which is surrounded both on the inside face 24 of the base via a circular setback 25, and on its outside face 26 by a tapering countersink 27 (FIG. 7). A wall 30 having a cylindrical inside surface 31 about the axis A and having a tapering outside surface 32 (FIGS. 5 and 7) is secured to the portion 22, thereby leaving a rim 33 for snap-fastening engagement of the housing 21. A radial lug 35 lying in the plane of the portion 22 projects out therefrom, while the wall 30 has a recess or guide 36 that is diametrically opposite to the lug 35 and that includes a catch or hook 37 at one of its ends and a sloping ramp 38 at its other end.

Figure 5:
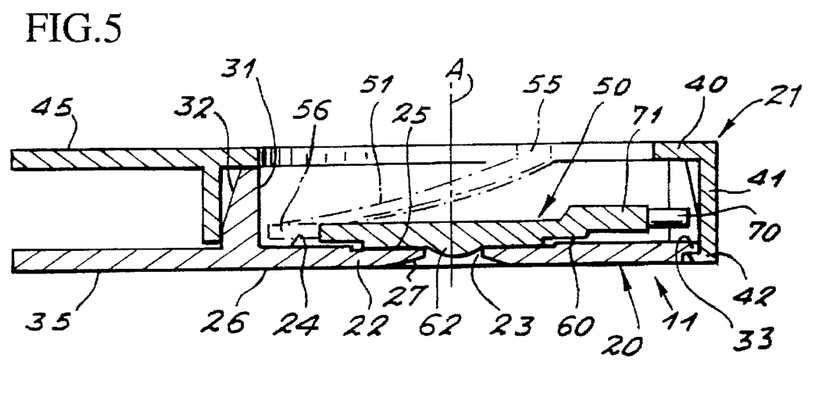
FIG. 5 is a diametral section view through a device of the above figures used on its own.
Figure 6:
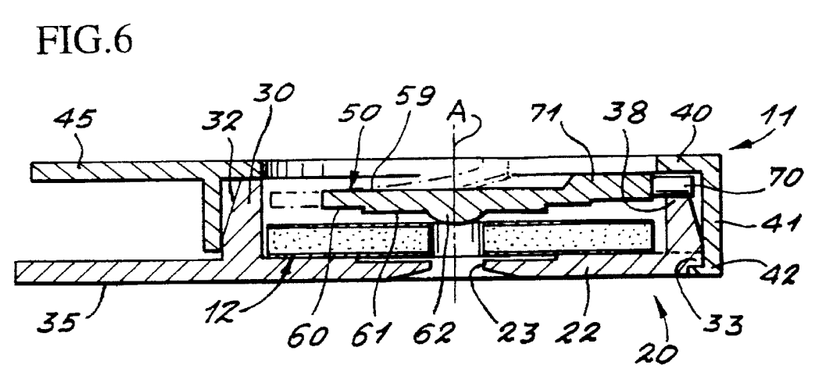
FIG. 6 is a section view on line 6—6 of FIG. 3 through a device of the above figures used together with a filter.

The cover 21 has the same circular outline as the base 20 and it includes an annular margin or edge 40 that is partially interrupted and that is about the same axis A as the base 20 when the two portions are connected together by engagement of the end 42 of a cylindrical wall 41 on the rim 33 (FIGS. 5 to 7); the engagement is such that the cover 21 can rotate relative to the base 20 about the axis A by applying driving force to a radial lug 45 that extends in the plane of the margin 40 away from its interrupted portion and outside said margin, the lugs 45 and 35 being substantially parallel when the device is assembled (FIGS. 5 to 7).

Figure 3:
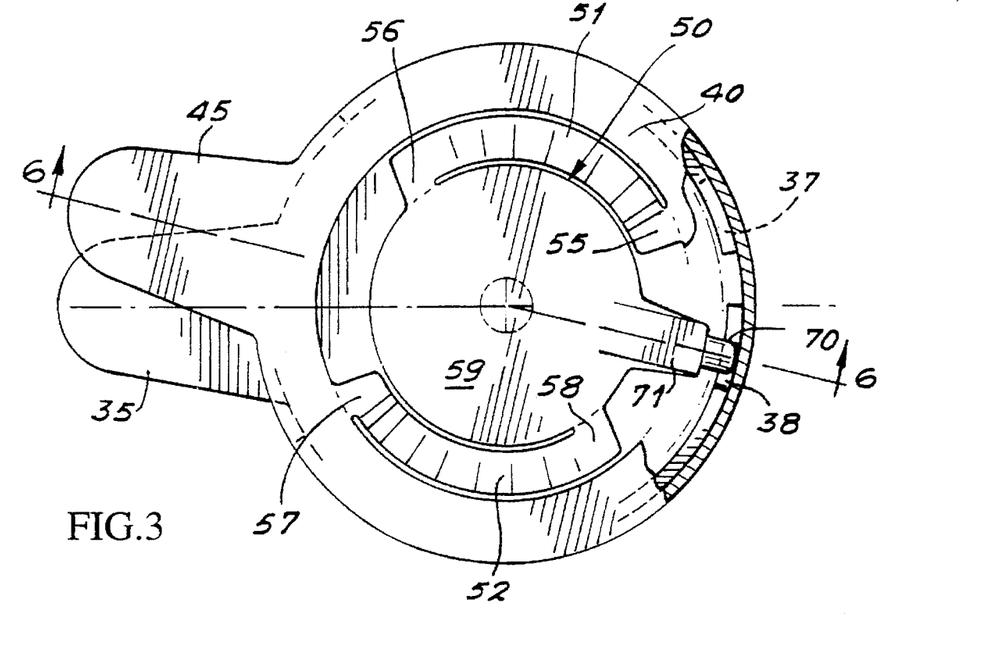
FIG. 3 is a partially cutaway plan view of the device of the preceding figures.
Figure 4:
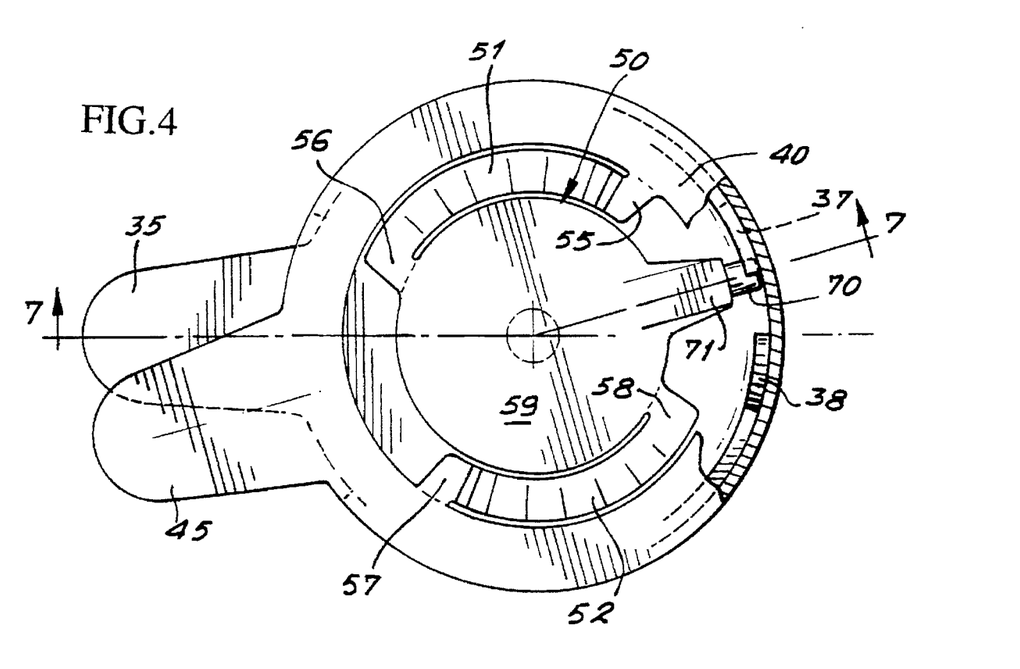
FIG. 4 is a view analogous to FIG. 3 but showing a different condition.

Inside the volume defined by the cylindrical wall 41 and the margin 40, the cover 21 includes a valve member 50 constituted by a closure member secured to two elastically deformable strips 51 and 52 (FIGS. 3 and 4) each of which is somewhat in the form of a helical arch that extends:

for the strip 51 between an end 55 level with the margin 40 and an end 56 level with the valve member 50; and for the strip 52 between an end 57 secured to the margin 40 and an end 58 secured to the valve member 50.

The rest position of the valve member is as shown in FIG. 5, i.e. it is in the vicinity of the free end 42 of the wall 41. It is generally circular in outline, having a face 52 facing towards the plane margin 40 while its opposite face 60 is shaped with a circular projection 61 that is complementary in shape to the setback 25 in the base 20. There is a bulge 62 in the form of a hemispherical bulge projecting from the center of the projection 61 and suitable for closing the opening 23 in the base 20 when said projection 61 is received in the setback 25 (as shown in FIG. 5). The valve member 50 thus constitutes a valve of the type that is closed at rest under resilient urging towards the inside face of the base, applying a predetermined return force that is exerted by the two deformable strips 51 and 52.

Said return force may be obtained directly during assembly of the base 20 and the cover 21 if said base and said cover are manufactured in the form of a single-piece blank having bridges of substance in the blank that connect together the base and the cover in such a manner that the distance between said cover 21 and the valve member 50 is greater than the final distance between the base 20 and the cover 21 as obtained in the housing 11 after said bridges of material have been broken on assembling together the base and the cover, the elastically deformable strips 51 and 52 always tending to return to the shape that they had in the blank which, for them, represents the rest state.

Substantially in line with the mean direction of the lug 45, the valve member 50 also includes a cylindrical finger 70 which forms the distal end of a portion 71 whose direction is thus radial and which is received facing the interrupted portion of the margin 40.

In accordance with the invention, the above-described device 10 can be used without a filter 12 (in which case it is in the condition shown in FIGS. 1 or 5 in the rest position), with its opening 23 in register with a hole t formed through the film $f_1$ of the bag P. The device can also be used, at the discretion of the patient, in association with a filter 12 which is placed prior to assembly between the base 20 and the cover 21, with the hole 15 of the filter being in register with the hole 23 in the base 20.

A device of the invention operates as follows:

WITHOUT FILTER

The housing 11 when closed and with its lugs 35 and 45 overlying each other is fixed to the bag P, the valve member 50 then being in the condition shown in FIG. 5, i.e. in the condition in which the circular projection 61 is received in the setback 25 and in which the hemispherical bulge 62 closes the opening 23. In this condition, the finger 70 is in the recess 36 and when the pressure of intestinal gases inside the bag P exceeds the predetermined return force exerted by the strips 51 and 52, the valve member is lifted for venting purposes, after which it returns to the closed position before the pressure inside the bag has dropped down to atmospheric pressure, and all this takes place without intervention on the part of the patient: by keeping the inside pressure at a value that remains in equilibrium with the return force exerted by the strips 51 and 52, it is guaranteed that the walls of the bag will not stick to each other. Operation is automatic.

When the lug 45 is rotated to bring the finger 70 beneath the catch 37, the valve member 50 is locked in its closed position and venting is prevented.

In contrast, when the finger 70 is caused to rotate in the opposite direction to that described above, i.e. when it is rotated in the direction of arrow g in FIG. 2, then the finger 70 engages the sloping ramp 38 so that co-operation between the finger 70 and the ramp lifts the valve member 50, thereby allowing gas that has been collected inside the bag P to escape so that the pressure inside the bag decreases: such depressurization is caused when the user requires it.

WITH FILTER

When a filter 12 is installed in the housing 11 (prior to the housing being closed, either during assembly of the device in the factory or else when the bag is in place on a patient), the filter is located between the base 20 and the valve member 50 so that the rest condition is that shown in FIG. 7 in which the hemispherical bulge 62 co-operates with the hole 15 in the filter so as to close said hole, while the opening 23 facing the hole 15 allows the gases collected by the bag to pass through the filter.

When the lugs 35 and 45 overlie each other, then the bag P is vented through the filter 12, and this continues so long as the pressure remains at a normal value, clamping of the filter 12 guaranteeing good sealing of the valve member when the valve is closed, the path followed by gases between the base 20 and the filter being impeded by the angle formed by the setback 25. When excess pressure appears, the valve member 50 is moved independently of any action taken by the patient, and after venting and consequent reduction of the pressure inside the bag to a value that is in equilibrium with the predetermined return force of the resilient strips 51 and 52, said strips bring the valve member 50 back against the filter.

When the lug 45 is rotated in the opposite direction to that shown by arrow g, so that the finger 70 is engaged beneath the catch 37, the gases collected by the bag P pass through the filter 12, with any massive escape of gas being prevented unless it is provoked by the patient.

In a manner analogous to that described above for operation without a filter, when the cover 21 is rotated by driving the lug 45 in the direction of arrow g, then the valve member 50 is lifted because the finger 70 co-operates with the ramp 38, thereby causing pressure to drop, under the control of the patient, with most of the collected gases passing through the opening 23 of the filter 12.

Figures 1, 8:
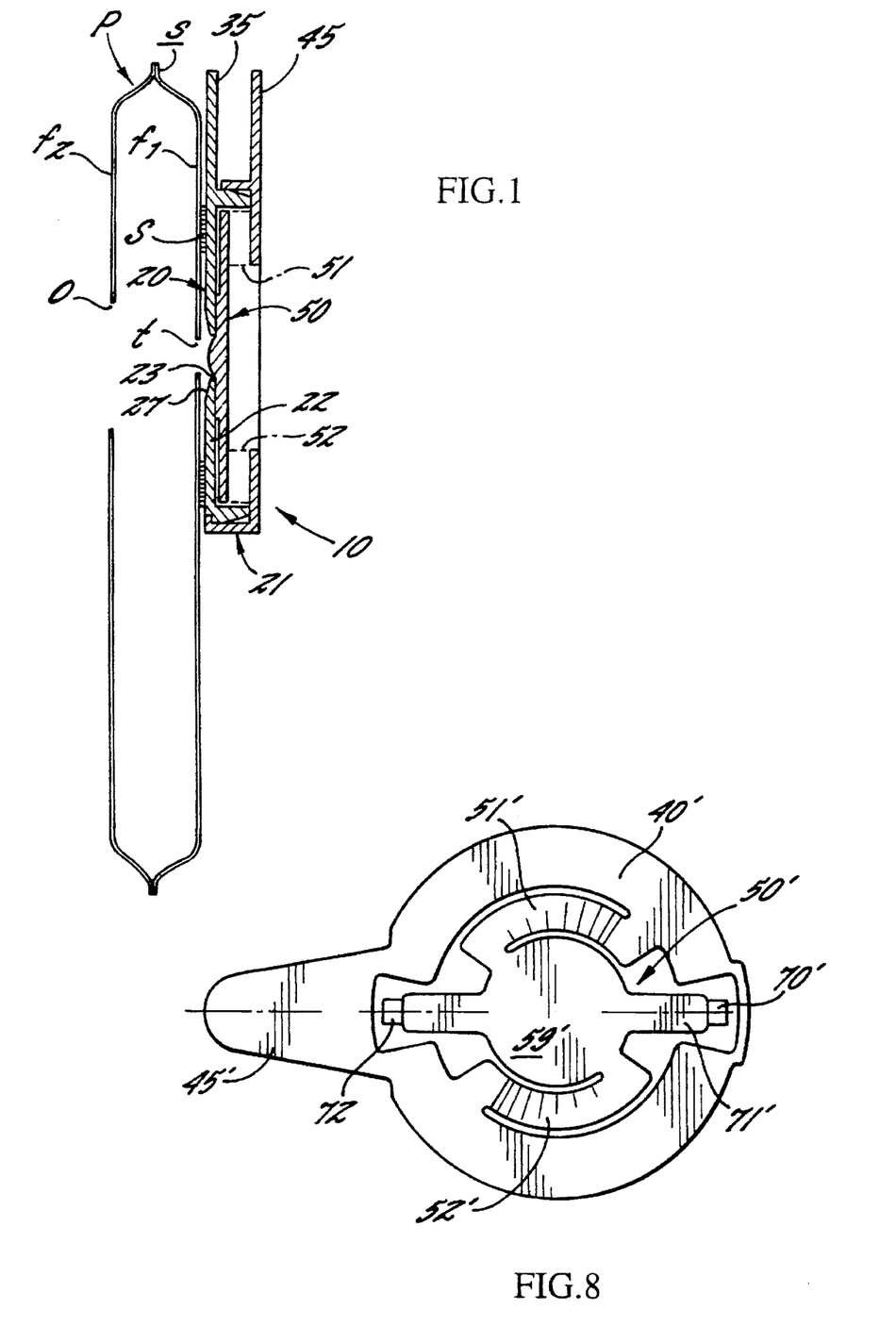
FIG. 1 is a diagrammatic section view of a first embodiment of a device of the invention associated with a collection bag.
FIG. 8 is a fragmentary plan view of a variant of the device of the above figures.

In the variant shown diagrammatically in FIG. 8, where portions corresponding to those already described are given the same reference numerals plus the prime symbol, the valve member 50' secured to two elastically deformable strips 51' and 52' includes two diametrically opposite fingers 70' and 72 that are each suitable for co-operating with a respective corresponding guide or recess in the base of the device. The operation of such a well-balanced embodiment is the same as that for the embodiment described above, with or without a filter.

The device of the invention is thus highly flexible in use, making it possible to satisfy the requirements of users or of medical personnel in order to take account of highly differing conditions in the use of the collection bag.

A second embodiment of the device 10 of the invention for venting and controlling the internal pressure of a stoma collection bag is shown in FIGS. 9 to 16. Elements analogous to those shown in the first embodiment have been given the same reference numerals.

Figure 9:
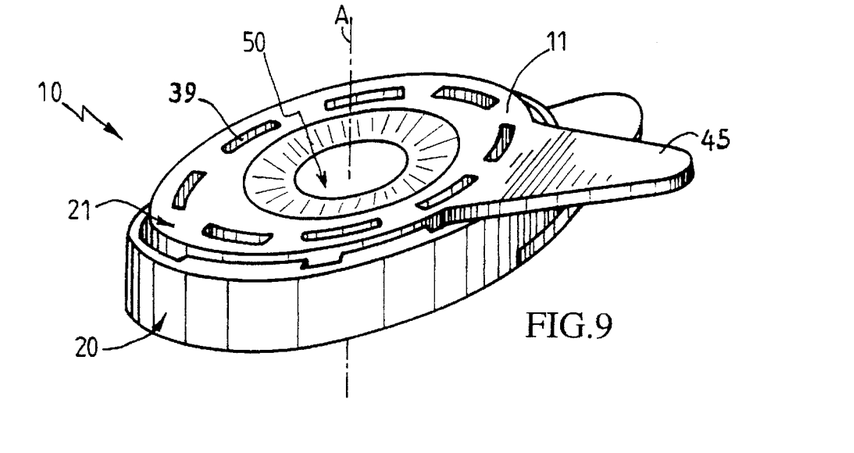
FIG. 9 is a perspective view of a second embodiment of the venting device of the invention in the form of a housing constituted by a base and by a cover.

FIG. 9 is a perspective view of the housing 11 constituting an embodiment of the device 10. The housing 11 is cylindrical about an axis A of circular symmetry. It is preferably made of a plastics material and is constituted by a base 20 and a cover 21 which fit advantageously one within the other. As better explained below, the base 20 includes an opening 23 (cf. FIG. 11) while the cover includes a valve member 50 adapted to co-operate with said opening 23 to open it or close it depending on how the gas pressure in the bag increases or decreases, and mainly when the user so desires.

Figure 10:
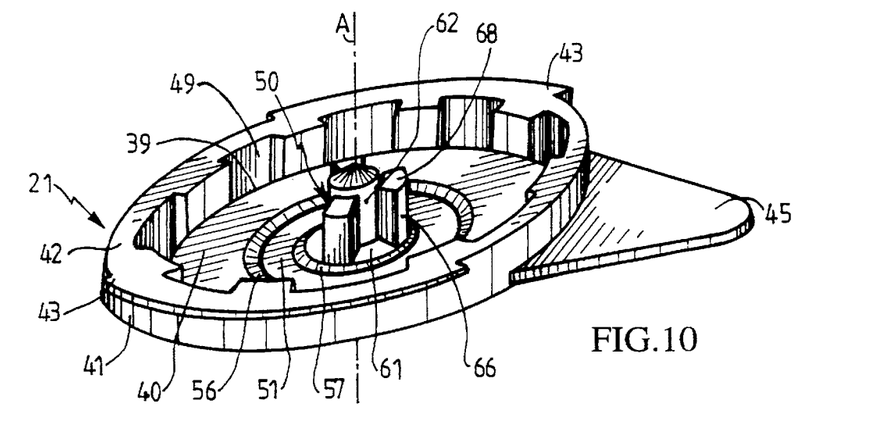
FIG. 10 is likewise a perspective view showing the cover of the FIG. 9 device, but compared with FIG. 9, the cover is shown upside-down.

The cover 21 is better seen in FIG. 10 which shows it the other way up so that the inside of the cover is visible. There can thus be seen a cylindrical wall 41 having a free end 42. At the opposite end of the wall 41 from said free end, a lug 45 projects radially outwards. The end 42 of the wall 41 is also provided with two outwardly projecting rims 43 each extending over its own sector. Each of them extends over a sector of about 90° and they are diametrically opposite. On the inside, axial recesses 49 (eight of them in the present case) are formed in the wall 41. The wall 41 surrounds a plane portion or margin 40 of the cover 21 that is in the form of a peripheral ring. Windows 39 formed through the margin 40 thus extend the axial recesses 49.

At the center of the cover 21 there can be found the valve member 50 which is constituted firstly by a ring 51 of material that is thinner than the margin 40. It is surrounded externally by a step 56 providing a transition between the margin 40 and the thinner ring 51. Similarly, the thinner ring 51 is bordered on the inside by another step 57. In this way, the ring 51 enables a disk 61 at the center of the valve member to move relative to the margin 40. The assembly comprising the margin 40, the thinner ring 51, and the disk 61 is molded in such a manner that when in the rest position, the disk 61 lies, relative to the plane of the margin 60, in a plane that is situated further into the cover 21. As a result, the thinner ring 51 performs the function of resilient means for urging the disk 61 towards the inside of the housing 11.

The closure member for the valve member 50 is also constituted by the disk 61 from which there projects a stud 62 surrounded by three lateral projections 66 that extend in directions that are at 120° intervals to one another. The stud 62 has a free end terminated by a tapering tip of a size selected to penetrate in part into the opening 23 and thereby close it. The tip projects from the free edges of the projections 66 which are themselves plane.

Figure 11:
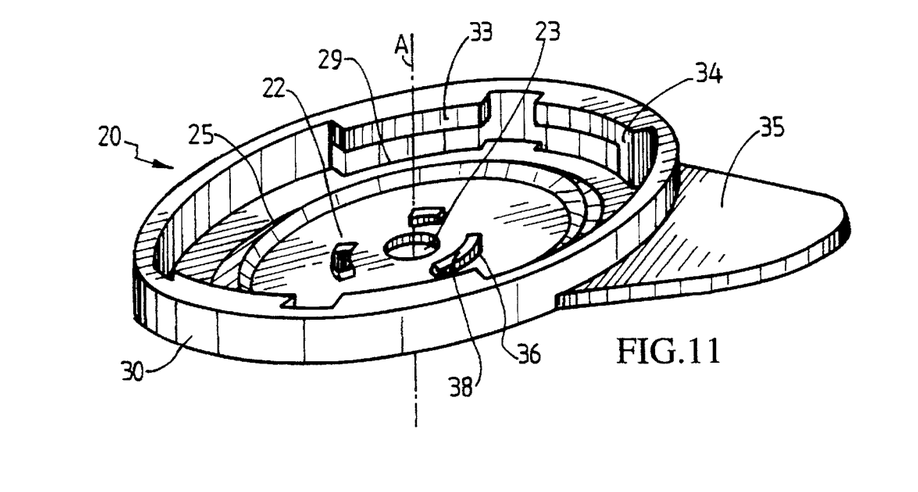
FIG. 11 is another perspective view showing the base of the FIG. 9 device.

The base 20 is shown in FIG. 11. It includes a cylindrical wall 30. A lug 35 extends radially outwards from a level opposite from the free end of the wall 30. Rims 33 extend radially inwards over respective sectors, level with said free end of the wall 30. Each of these sector rims occupies about 35°. There are two pairs of rims 33 each occupying a total sector of about 90°, which pairs are diametrically opposite. One of the rims 33 in each pair is extended by an axial column 34 that is integral with the wall 30.

The wall 30 of the base 20 surrounds a plane portion 22 which includes openings 29 disposed facing the rims 33. They are necessary for purposes associated with injection molding of the base 20. At the center of the plane portion 22 there is an opening 23 for communicating with the inside of the bag for stoma patients. As can be seen more clearly in the sections of FIGS. 13 and 14, in particular, the rim of the opening 23 inside the housing is provided with a sealing lip 27. An annular portion 25 in relief projects from the plane portion 22 roughly halfway between the cylindrical wall 30 and the opening 23. Three guides 36 in the form of helical ramps 38 project from the plane portion 22 of the base 20, e.g. in an anticlockwise direction, as shown, and disposed around the opening 23. They are designed to co-operate with the projections 66 of the valve member 50 when the base 20 and the cover 21 are mutually engaged to form the housing 11. Their radial distance from the axis A is thus equal to the radial distance of the projections 66 therefrom, and in this embodiment they are disposed like the projections 66 in directions that are at 120° intervals to one another.

The following figures serve to show more clearly how the cover 21 and the base 20 are engaged one within the other. The wall 41 of the cover 21 is received inside the wall 30 of the base 20. During engagement proper, it is necessary to present the sector rims 43 of the cover 21 in the empty gaps between the sector rims 33 of the base 20. Then, by rotating the cover 21 relative to the base 20, the rims 43 of the cover 21 are caused to pass beneath the rims 33 of the base 20 so that the cover 21 and the base 20 are fastened together by a bayonet-type fastening. The radial lugs 35 and 45 can be used to rotate the cover 21 relative to the base 20, the lugs thus serving as actuator means.

Once the parts have been engaged, the housing defines an inside space 19 which is suitable for receiving a filter. Although not shown in the figures, it is clear that once inserted inside the housing 11, the filter is clamped between the cover 21 and the base 20 essentially by the portion 25 in relief which is provided for this purpose.

Figure 12:
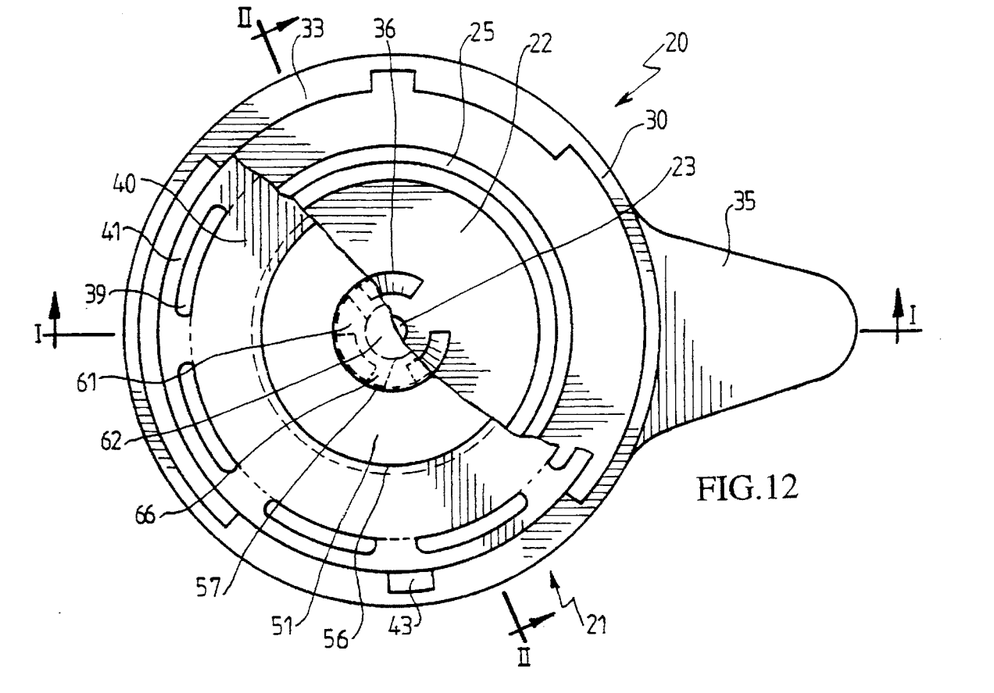
FIG. 12 is a plan view of the device in the valve-open position, the cover is shown partially cutaway so that a portion of the base is visible.
Figure 13:
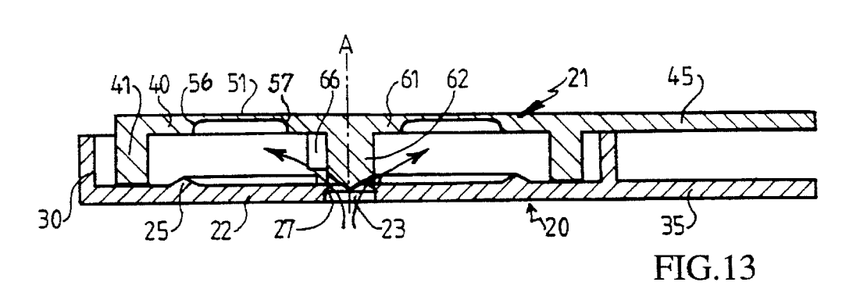
FIG. 13 is a section on plane I—I of FIG. 12 through the above device and in the same open position of the valve.
Figure 14:
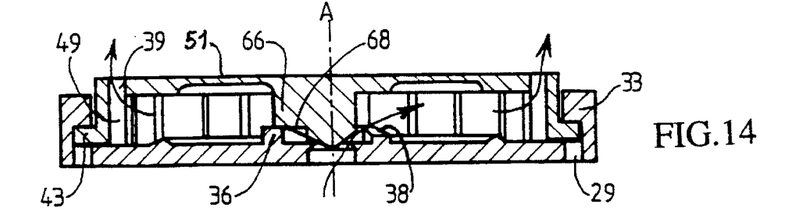
FIG. 14 is another section, this time on plane II—II of FIG. 12, showing the above device, still in the open position of the valve.

FIGS. 12 to 14 show the valve member 50 in its open position. In particular in the plan view of FIG. 12 where the projections 66 and the ramps 36 are shown in dashed lines, it can be seen that this position is achieved when the cover 21 and the base have been rotated relative to each other in such a manner that the ends 68 of the projections 66 bear against the topmost portions of the ramps 38, i.e. the cover is in its high position. Because of the flexibility of the thinner ring 51, this causes the tapering tip of the stud 62 to be withdrawn from the opening 23. Gas can thus escape through the opening 23 between the lip 27 and the tip following the arrows shown in FIGS. 13 and 14. Thereafter, gas is evacuated to the outside by passing through the windows 39 of the cover 21. If a filter is present in the inside space 19 of the housing 11, then the gases are constrained to pass through the filter. The gas makes its way to the windows 39 via the recesses 49 in the wall 41 that cannot be blocked by the filter because of their set-back shape.

Figure 15:
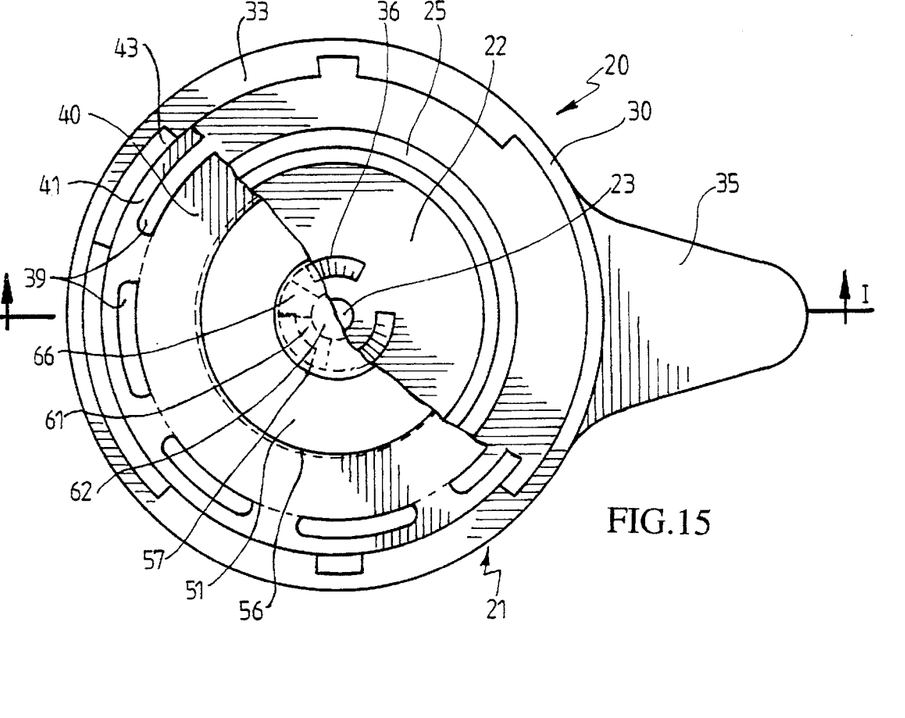
FIG. 15 is a plan view of the above device with its valve in the closed position.
Figure 16:
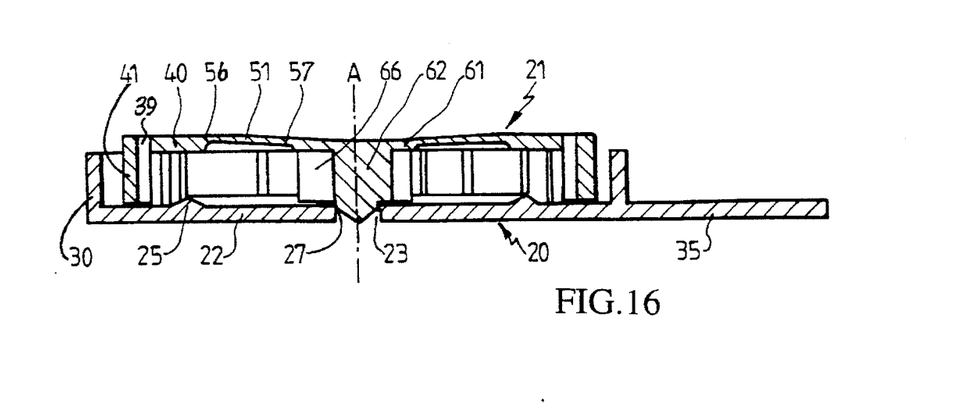
FIG. 16 is a section view on plane I—I of FIG. 15 showing the above device in the same valve-closed position.

FIGS. 15 and 16 show the closed position of the valve member 50. Under such circumstances, as can be seen clearly from the plan view of FIG. 15 where the projections 66 and the ramps 36 are again shown in dashed lines, the projections 66 now bear against the opposite ends of the ramps 38 of the guides 36, i.e. the cover is in its low position. As a result, the tapering tip of the stud 62 can penetrate into the opening 23. It is held therein by the return force provided by the resilient effect due to the way in which the assembly comprising the margin 40, the thinner ring 51, and the disk 61 is molded. In addition, co-operation between the tip and the lip 27 ensures that the closure is sealed. The column 34 situated at the end of a rim 33 acts as a stop to prevent the cover 51 being rotated too far relative to the base 20 and thus preventing the projections 66 from losing contact with the ramps 38.

In this low position, the valve member 50 is capable of opening automatically to some extent if the pressure of gas in the bag becomes so great that by acting on the tip through the opening 23 it manages to exert a force capable of overcoming the return force of the resilient means constituted by the thinner ring 51.

It should be observed that in the first embodiment of the present device, gas escapes through the filter when the valve member is closed, but when the valve is open it escapes directly through the opening 15 of the filter, i.e. without passing through the filter. In the second embodiment, closure of the valve member prevents any gas escaping and seals the bag, whereas when the valve member is open, gas is obliged to pass through the filter.

We claim:

1. A vent device configured to adapt to a stoma bag, said vent device comprising an essentially flat housing comprising: a base having a face inside the housing and a face outside the housing, said vent device being adapted to be fixed via said outside face to an exposed face of said bag and having an opening communicating with said bag, a cover configured to be removably assembled with said bag and to close said base when said cover and said base are assembled together, a valve which is closed at rest, the valve being formed by a valve member adapted to bear against the inside face of said opening in said base, said valve member being integral with said cover and being integral with resilient means for urging said valve member against said base with a predetermined return force, said resilient means being constituted by at least one resiliently deformable flat extending between said cover and said valve member, said housing being further provided with manual actuator means to place said valve member in a closed or opened position.

2. A vent device according to claim 1, wherein the distance between said cover and said valve member is greater than the distance between said base and said cover in said housing.

3. A vent device according to claim 1, wherein said housing includes an inside space for receiving a filter having a central hole in such a manner as to be clamped between said valve member and said base, the hole of said filter being in register with said opening through said base.

4. A vent device according to claim 1, wherein:
said housing is cylindrical; and
said cover is secured to said base in such a manner as to be displaced relative to said base by manual actuator means by rotation about the axis of the housing.

5. A vent device according to claim 4, wherein the cover is secured to the base by mutual engagement, and wherein the manual actuation means are constituted by a radially-projecting lug on the cover.

6. A vent device according to claim 5, wherein said base includes another radially-projecting lug suitable for serving as a position reference for the lug of the cover.

7. A vent device according to claim 4, wherein:
said valve member is secured to at least one radial finger suitable for moving, when said manual actuation means are actuated, along a circumferentially-extending guide of said base having a shape such that, depending on its position in said guide, said finger can be free or can be raised against said resilient means along a ramp of the guide.

8. A vent device according to claim 7, wherein there also exists a position in which said finger can be locked beneath a hook of said guide.

9. A vent device according to claim 4, wherein said valve member is constituted by a tapering tip, the cover also including at least one projection while said base includes at least one helical ramp on which said projection is suitable for traveling between a low position and a high position when the cover is rotated relative to said base in such a manner that, in the low position, said tapering tip is urged by the resilient means to close said opening whereas, in the high position, said tip is pushed away from the opening against said resilient means.

10. A vent device according to claim 5, wherein there are three projections and three ramps disposed in radial directions that are at 120° intervals relative to one another.

11. A vent device according to claim 10, wherein said projections are integral with a stud which carries said tapering tip at its end, the free ends of said projections being set back relative to said tip so that said tip penetrates into said opening when said projections are in their low position.

12. A vent device according to claim 9, wherein said housing includes an inside space suitable for receiving a filter and defined by a cylindrical wall including axial recesses communicating with top windows of the cover such that the gases can escape in spite of the presence of a filter inside the housing.

13. A vent device according to claim 12, wherein the base has an internal portion in relief adapted to clamp the filter in such a manner that the gases are constrained to pass through the filter in order to escape via the recesses and the windows.

14. A vent device according to claim 9, wherein the cover is secured to the base by a bayonet-type fastening.

15. A vent device according to claim 14, wherein said base and said cover have rims suitable for co-operating in such a manner that, once said base and said cover are engaged, said rims co-operate to prevent them from coming apart, said rims each extending over a sector of about 90° and being disposed diametrically opposite each other on the cover and on the base.

16. A device according to claim 15, wherein the cover penetrates inside the base, the rims of the cover projecting outwards while the rims of the base project inwards.

17. A vent device according to claim 14, wherein at least one rim is extended by an axial column acting as a stop to prevent the base and the cover rotating beyond a certain amount, thereby ensuring that the projections do not move off said respective ramps.

18. A collection system including a stoma collection bag and vent device comprising means defining a container for receiving and storing waste running from the stoma of a patient, said container including an opening configured to be put into communication with the stoma when the bag is applied to the body of said patient by means of an adhesive plate or a coupling system, said container further comprising a device for venting and controlling internal pressure, said vent device comprising an essentially flat housing comprising: a base having a face inside the housing and a face outside the housing, said vent device being adapted to be fixed via said outside face to an exposed face of said bag and having an opening communicating with said bag, a cover configured to be removably assembled with said bag and to close said base when said cover and said base are assembled together, a valve which is closed at rest, the valve being formed by a valve member adapted to bear against the inside face of said opening in said base, said valve member being integral with said cover and being integral with resilient means for urging said valve member against said base with predetermined return force, said resilient means being constituted by at least one resiliently deformable flat extending between said cover and said valve member, said housing being further provided with manual actuator means to place said valve member in a closed or open position.

19. A vent device configured to adapt to a stoma bag, said vent device comprising an essentially flat housing and comprising:

a base having a face inside the housing and a face outside the housing, adapted to be fixed via said outside face to an exposed face of said bag and provided with an opening communicating with said bag;

a cover adapted to be removably assembled with said base and to close said base when said cover and said base are assembled together;

a valve which is closed at rest which includes a valve member adapted to bear against the inside face of said opening in said base and being integral with resilient means for urging said valve member against said base with a predetermined return force, said valve member being integral with said cover; and said housing further comprising rotational guide means for rotating said cover relative to said base around the axis of said housing between a first position in which the valve is closed and a second position in which the valve is opened.

* * * * *

UNITED STATES PATENT AND TRADEMARK OFFICE
CERTIFICATE OF CORRECTION

PATENT NO. : 5,626,569

DATED : May 6, 1997

INVENTOR(S) : Henri Holtermann et al.

It is certified that error appears in the above-identified patent and that said Letters Patent is hereby corrected as shown below:

Column 10, line 56, "claim 5" should be --claim 9--.

Signed and Sealed this

Twenty-eighth Day of October, 1997

*Attest:*

BRUCE LEHMAN

*Attesting Officer*     Commissioner of Patents and Trademarks